United States Patent [19]

Taylor

[11] 3,997,602

[45] Dec. 14, 1976

[54] PRODUCTION OF ACETIC ACID USING A VANADIUM TETROXIDE/NON-POROUS SILICA CO-CATALYST COMPOSITION

[75] Inventor: Paul D. Taylor, Clinton, N.J.

[73] Assignee: Celanese Corporation, New York, N.Y.

[22] Filed: Nov. 25, 1974

[21] Appl. No.: 526,659

[52] U.S. Cl. .......................................... 260/533 R
[51] Int. Cl.² ........................................ C07C 51/20
[58] Field of Search ............................... 260/533 R

[56] References Cited
FOREIGN PATENTS OR APPLICATIONS 166,670   12/1963   U.S.S.R. ...................... 260/533 R

OTHER PUBLICATIONS

Chem. Abstracts, V. 42:857 (1948).

*Primary Examiner*—Vivian Garner

[57] ABSTRACT

There is provided a process for preparing acetic acid by the vapor phase oxidation of lower aliphatic hydrocarbons such as butane. This process comprises reacting the lower aliphatic hydrocarbon and an oxygen-containing gas in the vapor phase in the presence of steam and a catalytic amount of a co-catalyst composition of vanadium tetroxide and finely divided, non-porous silica particles.

10 Claims, No Drawings

PRODUCTION OF ACETIC ACID USING A VANADIUM TETROXIDE/NON-POROUS SILICA CO-CATALYST COMPOSITION

BACKGROUND OF THE INVENTION

Processes for producing lower aliphatic monocarboxylic acids such as acetic acid by the vapor phase oxidation of lower aliphatic hydrocarbons such as butane are known. For example, acetic acid is prepared by the vapor phase oxidation of butane according to the following equation: $C_4H_{10} + 5/2\ O_2 \rightarrow 2CH_3COOH + H_2O$. Such processes frequently involve the use of catalysts, as shown for example in Russian patent No. 166,670, which discloses such a process utilizing a vanadium pentoxide catalyst.

The use of vanadium pentoxide catalysts, either supported or unsupported, for the vapor phase oxidation of lower aliphatic hydrocrabons results in yields and process efficiency which fall substantially short of theoretical potential. Also, the resulting products are often impure due to a lack of selectivity when such processes are employed.

Neat (i.e. unsupported) vanadium tetroxide has been suggested as a remedy for the above disadvantages but the use of this catalyst in the vapor phase oxidation of lower aliphatic hydrocarbons also results in inefficient processes which lack a high degree of selectivity. Further, neat vanadium tetroxide lacks the physical strength of a supported catalyst and also lacks sufficient heat transfer characteristics for this highly exothermic reaction. Accordingly, hot spots are produced in the catalyst bed during a vapor phase oxidation.

In addition, when using neat vanadium tetroxide, it is necessary to maintain a careful balance between temperature and the ratio of lower aliphatic hydrocarbon to oxygen in order to prevent the neat catalyst from being oxidized to vanadium pentoxide.

Another problem which occurs when neat vanadium tetroxide is used as a catalyst for the vapor phase oxidation of lower aliphatic hydrocarbons is that substantially all (i.e., more than 75 percent) of the total conversion occurs in the first portion of the catalyst zone or bed (i.e., the first 25 percent of the total catalyst zone or bed) which is in contact with the reactants. This concentration of conversion in the first portion of the zone in an exothermic reaction raises the exotherm temperature at that point substantially in excess of that at later points in the catalyst zone. These high exotherm temperatures make control of the reaction more difficult, dictate more expensive heatresistant materials, often decrease the yield of desired product and/or increase the yield of undesired by-products and are otherwise disadvantageous.

OBJECTS AND SUMMARY OF THE INVENTION

Accordingly, a general object of the present invention is to avoid or substantially alleviate the above problems of the prior art.

A more specific object is the provision of a process for the production of acetic acid by the vapor phase oxidation of lower aliphatic hydrocarbons.

A further object is to provide a highly efficient process for the production of acetic acid by the vapor phase oxidation of lower aliphatic hydrocarbons.

Still another object of the present invention is to provide a process for the production of acetic acid by the vapor phase oxidation of lower aliphatic hydrocarbons wherein a relatively even exotherm temperature is maintained throughout the reaction zone.

Another object is to provide a process for the production of acetic acid by the vapor phase oxidation of lower aliphatic hydrocarbons using a catalyst which has improved physical strength.

Yet another object is to provide a process for the production of acetic acid by the vapor phase oxidation of lower aliphatic hydrocarbons using a catalyst which is comparatively insensitive to the balance of reactor temperature and the ratio of lower aliphatic hydrocarbon to oxygen.

These and other objects are achieved by a process for preparing acetic acid by the vapor phase oxidation of a lower aliphatic hydrocarbon such as butane, which process comprises reacting the lower aliphatic hydrocarbon and an oxygen-containing gas in the vapor phase in the presence of steam and a catalytic amount of a co-catalyst composition of vanadium tetroxide and finely divided, non-porous silica particles.

The essence of the present invention is the discovery that the above-noted co-catalyst composition of vanadium tetroxide and finely divided, non-porous silica has been found to catalyze the oxidation of a lower aliphatic hydrocarbon such as butane to acetic acid more efficiently than catalysts such as neat vanadium tetroxide. For example, in the vapor phase oxidation of butane to acetic acid, an increase in efficiency of nearly 10 percent (of theoretical yield) is realized when the co-catalyst composition of vanadium tetroxide and finely divided, non-porous silica particles is used rather than neat vanadium tetroxide.

This co-catalyst composition also has improved heat transfer characteristics over neat vanadium tetroxide.

Other objects and advantages of the present invention will become apparent from the following description of the preferred embodiments of the present invention.

DESCRIPTION OF THE PREFERRED EMBODIMENTS

The finely divided, non-porous silica particles of the present invention can be prepared, for example, by the hydrolysis of silicon tetrachloride at elevated temperatures, e.g., 1100° C. Such high temperature hydrolysis results in non-porous silica which has an external surface area of generally from about 1 to about 500, typically from about 25 to about 350, and preferably from about 100 to about 200, square meters per gram and a particle size of generally from about 0.001 to about 1.0, typically from about 0.005 to about 0.5, and preferably from about 0.01 to about 0.1 microns. This non-porous silica employed in the process of the present invention is commercially available, for example, from the Cabot Corporation under the trade name Cab-O-Sil. Fumed silica (i.e., a fine white powdered form of silica made by combustion of silicon tetrachloride in hydrogen-oxygen furnaces), available commercially from Degussa Inc., is also suitable.

The non-porous silica acts as a heat sink which aids in the removal of heat from the catalyst as well as reduces the concentration of catalyst sites per volume. Thus, the same heat of reaction is spread over a larger volume than it would be if the vanadium tetroxide were not mixed with the silica.

The vanadium tetroxide is preferably obtained through calcination of an aqueous solution of a water-soluble vanadium salt. This aqueous solution of the water-soluble vanadium salt may in general contain any proportion of water and vanadium salt as long as the solubility of the vanadium salt is not substantially exceeded. A high concentration of vanadium salt is generally preferred however in order to minimize evaporation. Thus generally the aqueous solution contains from about 2 to about 65, typically from about 20 to about 60, and preferably from about 40 to about 50 percent by weight vanadium salt and correspondingly may generally contain from about 35 to about 98, typically from about 40 to about 80, and preferably from about 45 to about 60 percent by weight water based upon the total weight of the aqueous solution.

The manner in which the finely divided non-porous silica is produced and the manner in which the vanadium tetroxide is produced are well known and are not per se part of the present invention.

The co-catalyst composition of the present invention may be prepared in any convenient manner, for example, in any of the following ways.

1. The finely divided, non-porous silica particles are intimately mixed with an aqueous solution of a water-soluble vanadium salt (such as vanadyl oxalate) which is decomposable by heat to vanadium tetroxide. This co-catalyst mixture is dried under nitrogen at elevated temperatures, and the solid co-catalyst is calcined by prolonged heating at high temperatures, e.g., from about 200° to about 600° C, in an inert gas stream, e.g., nitrogen, or other inert gases, in the substantial absence of molecular oxygen.

2. The same process as above may be used except that an aqueous suspension of colloidal silica particles (such as Ludox AS) may be substituted for the non-porous silica particles used above.

3. The co-catalyst composition of the present invention may also be prepared as described in co-pending U.S. patent application Ser. No. 526,986, now U.S. Pat. No. 3,962,137, which is hereby incorporated by reference. The process described in this copending application results in an especially abrasion resistant co-catalyst composition comprising a metal oxide and non-porous colloidal silica particles. This process comprises (a) intimately mixing an aqueous suspension of colloidal silica particles (such as Ludox AS) with an aqueous solution of a water-soluble metal salt (such as vanadyl oxalate) which is decomposable by heat to a metal oxide, (b) calcining this mixture to form a metal oxide (such as vanadium tetroxide) and non-porous colloidal silica containing co-catalyst composition, (c) adding further aqueous suspension of colloidal silica particles to the calcined co-catalyst composition of step (b), and (d) drying this composite co-catalyst.

This latter method results in a co-catalyst composition of increased abrasion resistance.

The co-catalyst particles produced in the process of the present invention will be larger than the individual non-porous colloidal silica particles because the colloidal silica particles tend to agglomerate when the catalyst composition is calcined. Thus, generally the co-catalyst particles will be larger than $10^{-7}$ centimeters (0.001 microns), typically from about $10^{-4}$ centimeters to about 2 centimeters. For example, when a fluidized bed reactor is used, particles of from about 0.001 to about 0.01, perferably from about 0.003 to about 0.008, centimeters are employed whereas when a fixed bed reactor is used, particles of from about 0.1 to about 1.5, preferably from about 0.2 to about 1.3 centimeters are employed. It will be understood that other shapes and sizes may be utilized depending upon the particular reaction, reactor, and reaction conditions.

Usually, the particles resulting from a given calcination will be a mixture of all sizes of co-catalyst particles. The calcined composition may be screened, sieved, or otherwise treated to segregate the mixture into co-catalyst particles of appropriate size, which size can be widely varied as noted above.

These co-catalyst particles have a surface area of generally from about 20 to about 75, typically from about 30 to about 60, and preferably from about 40 to about 50 square meters per gram.

The co-catalyst composition of vanadium tetroxide and non-porous silica can be of widely varying proportions, although vanadium tetroxide is generally present from about 25 to about 98, typically from about 50 to about 95, preferably from about 65 to about 90, percent by weight of the total co-catalyst composition and the non-porous silica is correspondingly generally present in an amount of from about 2 to about 75, typically from about 5 to about 50, and preferably from about 10 to about 35, percent by weight of the total co-catalyst composition.

The co-catalyst composition of the present invention has greater physical strength (or greater "crush" strength) than that of neat vanadium tetroxide. It has been found that neat vanadium tetroxide is extremely friable and tends to break apart under the conditions of the present process. In contradistinction thereto, the particular composition of vanadium tetroxide and non-porous silica of the present invention is extremely resistant to breaking or crumbling, even at elevated temperatures and pressures.

As indicated hereinabove, in the process of the present invention a lower aliphatic hydrocarbon is reacted with an oxygen-containing gas in the presence of a catalytically effective amount of the above-defined catalyst to produce acetic acid. By "lower aliphatic hydrocarbon" is meant any saturated or unsaturated aliphatic hydrocarbon containing from 2 to 20 carbon atoms. These lower aliphatic hydrocarbons include alkanes, alkenes, and alkynes. Particularly preferred aliphatic hydrocarbons are the alkanes including ethane, propane, butane, isobutane, octane, isododecane and mixtures thereof.

The production of acetic acid from butane can give particularly advantageous results.

The oxygen necessary as a reactant in the present process may be from practically any molecular oxygen-containing gas such as molecular oxygen or air. Also, the molecular oxygen-containing gas may be one wherein molecular oxygen is mixed in varying amounts with an inert diluent gas such as nitrogen, argon, or a carbon oxide.

The lower aliphatic hydrocarbon and oxygen-containing gas can be reacted within a wide range of molar ratios. However, it is preferred that a large excess of hydrocarbon be used — i.e., the molar ratio of oxygen to lower aliphatic hydrocarbon should be about 1:1 or less, for example, from about 1:1 to about 0.05:1, typically from about 0.8:1 to about 0.1:1, and preferably from about 0.33:1 to about 0.16:1.

The present process should preferably be carried out in the presence of steam. It has been found that when conducting the present process in the absence of steam up to about 50 percent of the product formed is maleic anhydride rather than acetic acid. The lower aliphatic hydrocarbon and steam can be introduced into the reactor in any molar ratio, but a molar ratio of steam to lower aliphatic hydrocarbon of generally from about 0.1:1 to about 5.0:1, typically from about 0.5:1 to about 2:1, and preferably from about 0.8:1 to about 1.2:1 is employed.

The present process is carried out at a temperature generally between about 100° and about 400° C, typically between about 200° and about 350° C, and preferably between about 220° and about 300° C.

The present process can be carried out at subatmospheric, atmospheric, or superatmospheric pressures, generally from about 0.1 to about 50 atmospheres, typically from about 0.5 to about 30 atmospheres, and preferably from about 1 to about 15 atmospheres.

The contact time of the reactants with the co-catalyst composition is generally between about 0.1 and 100 seconds, typically between about 1 and 50 seconds, and preferably between about 5 and 15 seconds. By contact time as used herein, is meant the contact time adjusted to 25° C and 1 atmosphere pressure (i.e., standard temperatre and pressure, denoted by STP). Thus the contact time is calculated by dividing the volume of the catalyst bed (including voids) by the volume per unit time flow rate of the reactants at STP.

The process of the present invention may be carried out continuously and the co-catalyst may be present in various forms such as in one or more fixed beds or as a fluidized system.

Portions of the reactants which do not undergo reaction may be recycled if necessary. The desired acetic acid product may be separated from any impurities by condensation followed by fractionation and aqueous or non-aqueous extraction of the product from the unreacted lower aliphatic hydrocarbon.

In this specification, the terms conversion and efficiency are defined as follows:

$$\text{Conversion, \%} = \frac{\text{moles lower aliphatic hydrocarbon or oxygen converted}}{\text{moles lower aliphatic hydrocarbon or oxygen fed}} \times 100$$

$$\text{Efficiency, \%} = \frac{\text{moles acetic acid produced}}{\text{theoretical moles acetic acid produced}} \times 100$$

Acetic acid is generally produced by the present process with a conversion (based on oxygen) generally of at least about 85 percent, typically at least about 90 percent, often at least about 95 percent, a conversion based on lower aliphatic hydrocarbon (which, as noted above, is present in substantial excess) generally of at least about 1 percent, typically at least about 3 percent, often at least about 5 percent, and an efficiency of generally at least about 50 percent, typically at least about 55 percent, often at least about 60 percent.

As indicated hereinabove, the present process is useful for preparing acetic acid with improved yield and process efficiency. The use of the co-catalyst composition of vanadium tetroxide and finely divided, non-porous silica in the process of the present invention is also advantageous because of its improved physical strength over neat vanadium tetroxide.

The present invention is further illustrated by the following examples. All parts and percentages in the examples as well as in the specification and claims are by weight unless otherwise specified.

EXAMPLE I

This example illustrates the preparation of a co-catalyst composition of vanadium tetroxide and non-porous silica, and also illustrates the difference between the use of this co-catalyst composition and that of neat vanadium tetroxide in the vapor phase oxidation of butane to acetic acid.

A solution of vanadyl oxalate is prepared by dissolving 50 grams of vanadyl oxalate in enough water to bring the total volume to 70 milliliters. Eight grams of non-porous silica particles (having an average particle size of about 0.012 microns) is admixed with this solution in a Banbury mixer for 15 minutes to form a mixture of about 75 weight percent vanadium tetroxide and 25 weight percent silica. The mixture is then dried for 16 hours under nitrogen gas at 100° C and the solid is calcined in a 1-inch glass tube by heating initially at about 150° C for 0.5 hours and then at about 400° C for about 4 hours in a nitrogen stream. The co-catalyst composition is then allowed to cool at room temperature before being removed from the calcining tube. The nitrogen flow is continued during cooling.

The co-catalyst particles have an average particle size of about −20+30 mesh (about 500 to 775 microns). This co-catalyst mixture is used in Runs 1 and 2.

A series of runs are made under varying conditions of temperature and contact time utilizing this co-catalyst composition in the vapor phase oxidation of butane to acetic acid in an amount of 10 milliliters of co-catalyst in a 0.5 inch stainless steel pipe reactor in a fluidized sand bath. The feed composition is held constant throughout the run. The molar ratio of oxygen to butane in the feed is about 0.2:1 and the molar ratio of steam to butane is 1:1. The runs are conducted at atmospheric pressure and involve a total time of about 72 hours. At the end of this period, the co-catalyst composition is still active and has not changed significantly in physical appearance. Representative results of these runs are shown in Table I below as Run Nos. 1 and 2.

TABLE I

| Run No. | Temp. (° C.) | Contact Time, Sec.(STP) | Conversion Percent $O_2$ | $C_4H_{10}$ | Efficiency |
|---|---|---|---|---|---|
| 1 | 223 | 9.8 | 88 | 5.5 | 67.0 |
| 2 | 226 | 9.8 | 93 | 5.7 | 66.0 |

The following runs 3 to 5 are made under identical conditions as runs 1 and 2 above except that neat vanadium tetroxide, (produced by vanadyl oxalate decomposition) is used as the catalyst. The vanadium tetroxide particles have an average particle size of about −20+30 mesh (about 500 to about 775 microns).

TABLE II

| Run No. | Temp. (° C.) | Contact Time, Sec. (STP) | Conversion Percent $O_2$ | $C_4H_{10}$ | Efficiency |
|---|---|---|---|---|---|
| 3 | 240 | 9.2 | 99 | 5.0 | 58 |
| 4 | 242 | 9.4 | 99 | 5.3 | 56 |
| 5 | 237 | 9.1 | 99 | 4.9 | 59 |

As can be seen from the above runs, the use of the co-catalyst composition of vanadium tetroxide and finely divided non-porous silica results in a more efficient process as well as a higher butane conversion in preparing acetic acid than when neat vanadium tetroxide is used as catalyst.

In addition, data collected during the runs show that the co-catalyst mixture results in a more evenly distributed temperature profile along the catalyst bed with reduction of maximum exotherm temperature. Finally, the co-catalyst mixture does not crumble as does the neat vanadium tetroxide catalyst. The "crush" strength of the neat vanadium tetroxide at the conclusion of the runs is less than about one third that of the fresh catalyst whereas the calcined vanadium tetroxide/silica co-catalyst mixture has just as high a crush strength at the end of the run as it had at the beginning.

EXAMPLE II

Acetic acid is produced by the vapor phase oxidation of butane in the presence of various catalyst mixtures under substantially identical reaction conditions. In each run, butane, oxygen (molar ratio of oxygen to butane of 0.2:1) and steam (molar ratio of steam to butane of about 1:1) are reacted at a pressure of 1 atmosphere and a contact time of 9 seconds (STP). The runs are each carried out for a total reaction time of 36 hours. The catalyst composition in each case has an average particle size of −20+30 mesh (about 500 to 775 microns).

Each of catalysts, A, B and C is prepared by mixing an aqueous solution of vanadyl oxalate with sufficient solid particles to form, after drying and calcining, a 75/25 weight percent mixture of vanadium tetroxide and solid particle material. The solid particle material of catalyst A is an anhydrous, non-porous silica having an average particle size of 0.012 microns while the solid particle material of catalyst B is porous silica particles having an average particle size of about −20+30 mesh and the solid particle material of catalyst C is non-porous silica-alumina particles (containing 87 weight percent silica) having an average particle size of about −20 +30 mesh.

The percent conversion and percent efficiency are measured for each run and are shown below in Table III.

TABLE III

| Run No. | Catalyst | Temperature °C | Conversion Percent | | Efficiency |
|---|---|---|---|---|---|
| | | | $O_2$ | $C_4H_{10}$ | |
| 6 | A | 245 | 99 | 6.0 | 60 |
| 7 | B | 263 | 97 | 4.1 | 50 |
| 8 | C | 277 | 99 | 5.0 | 46 |

These runs show that the process of the present invention (Run 6) is an efficient process for the production of acetic acid by the vapor phase oxidation of a lower aliphatic hydrocarbon and that the particular type of silica used herein in conjunction with the vanadium tetroxide functions as a co-catalyst in the process of the present invention.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

I claim:

1. A process for preparing acetic acid by the vapor phase oxidation of butane which process comprises reacting said butane and an oxygen-containing gas in the vapor phase in the presence of steam and a catalytic amount of a co-catalyst composition of vanadium tetroxide and finely divided, non-porous silica particles wherein said co-catalyst composition consists essentially of from about 50 to about 95 percent by weight vanadium tetroxide and from about 5 to about 50 percent by weight non-porous silica particles.

2. The process of claim 1 wherein the molar ratio of oxygen to butane is from about 0.8:1 to about 0.1:1 and wherein the molar ratio of steam to butane is from about 0.5:1 to about 2:1.

3. The process of claim 2 wherein the contact time is from about 1 to about 50 seconds.

4. The process of claim 3 wherein the catalyst particles have an average particle size of about 0.001 to about 0.01 centimeters.

5. The process of claim 4 wherein said process is carried out at a temperature of from about 200 to about 350° C and at a pressure of from about 0.5 to about 30 atmospheres.

6. The process of claim 5 wherein said silica particles have a particle size of from about 0.001 micron to about 1 micron.

7. The process of claim 6 wherein the oxygen-containing gas is oxygen.

8. A process for preparing acetic acid by the vapor phase oxidation of butane which comprises (a) reacting said butane with air such that the molar ratio of oxygen contained in said air to butane is from about 0.33:1 to about 0.16:1 at a temperature of from about 220° to about 300° C and at a pressure of from about 1 to about 15 atmospheres with a contact time of from about 5 to about 15 seconds in the presence of steam and a co-catalyst composition, said co-catalyst composition consisting essentially of from about 65 to about 90 percent by weight vanadium tetroxide and from about 10 to about 35 percent by weight finely divided non-porous silica having a particle size from about 0.001 micron to about 1 micron, and (b) recovering the acetic acid.

9. The process of claim 8 wherein the molar ratio of steam to butane is from about 0.8:1 to about 1.2:1.

10. The process of claim 9 wherein the co-catalyst particles have an average particle diameter of about 0.1 to about 1.5 centimeters.

* * * * *